(12) United States Patent
Masaoka et al.

(10) Patent No.: US 9,636,490 B2
(45) Date of Patent: May 2, 2017

(54) MICRONEEDLE

(75) Inventors: Koichi Masaoka, Osaka (JP); Keizo Ikari, Osaka (JP); Takashi Oda, Osaka (JP); Katsunori Kobayashi, Kagawa (JP); Hidetoshi Hamamoto, Kagawa (JP); Masaki Ishibashi, Kagawa (JP); Kiyotsuna Toyohara, Tokyo (JP)

(73) Assignee: MEDRX CO., LTD., Kagawa (JP)

( * ) Notice: Subject to any disclaimer, the term of this patent is extended or adjusted under 35 U.S.C. 154(b) by 912 days.

(21) Appl. No.: 13/881,322

(22) PCT Filed: Oct. 24, 2011

(86) PCT No.: PCT/JP2011/075013
§ 371 (c)(1),
(2), (4) Date: Jul. 16, 2013

(87) PCT Pub. No.: WO2012/057345
PCT Pub. Date: May 3, 2012

(65) Prior Publication Data
US 2013/0296790 A1 Nov. 7, 2013

(30) Foreign Application Priority Data
Oct. 25, 2010 (JP) .................. 2010-238663

(51) Int. Cl.
*A61M 5/00* (2006.01)
*A61M 37/00* (2006.01)

(52) U.S. Cl.
CPC . *A61M 37/0015* (2013.01); *A61M 2037/0023* (2013.01); *A61M 2037/0053* (2013.01); *A61M 2037/0061* (2013.01)

(58) Field of Classification Search
CPC .. A61M 2037/0023; A61M 2037/0053; A61M 2037/0061; A61M 37/0015
(Continued)

(56) References Cited

U.S. PATENT DOCUMENTS

| 6,451,240 B1 | 9/2002 | Sherman et al. |
| 2002/0020688 A1 | 2/2002 | Sherman et al. |

(Continued)

FOREIGN PATENT DOCUMENTS

| JP | 2006-96002 | 4/2006 |
| JP | 2007-89792 | 4/2007 |

(Continued)

OTHER PUBLICATIONS

Office Action issued Sep. 30, 2014 in corresponding Chinese patent application No. 201180051191.9.
(Continued)

*Primary Examiner* — Jason Flick
(74) *Attorney, Agent, or Firm* — Wenderoth, Lind & Ponack, L.L.P.

(57) ABSTRACT

A microneedle and a microneedle array, which have both aspects of safety and easiness to use and can administer a predetermined dose of a medical agent without causing a pain by smoothly running into the skin surface layer of a patient, includes a frustum and a forward end portion thereon, the forward end portion having a forward end apex angle in the range of 15 to 60° and a forward end diameter in the range of 1 to 20 μm and satisfying the expression H/D≥5, where H is a total height of the microneedle, and D is a diameter of a bottom surface of the frustum).

17 Claims, 9 Drawing Sheets

(58) Field of Classification Search
USPC .......................................................... 604/173
See application file for complete search history.

(56) References Cited

U.S. PATENT DOCUMENTS

| | | | | |
|---|---|---|---|---|
| 2005/0261632 | A1* | 11/2005 | Xu | A61K 9/0021 604/173 |
| 2008/0221532 | A1 | 9/2008 | Ogawa | |
| 2008/0287858 | A1 | 11/2008 | Duan | |
| 2011/0270221 | A1* | 11/2011 | Ross | A61B 17/205 604/506 |
| 2011/0313298 | A1* | 12/2011 | Rylander | A61B 5/0059 600/478 |
| 2013/0110078 | A1* | 5/2013 | Moore | A61K 39/00 604/506 |

FOREIGN PATENT DOCUMENTS

| | | |
|---|---|---|
| JP | 2007-130030 | 5/2007 |
| JP | 2007-130417 | 5/2007 |
| JP | 2007-190112 | 8/2007 |
| JP | 2008-142183 | 6/2008 |
| JP | 2009-254756 | 11/2009 |
| JP | 2010-29634 | 2/2010 |
| WO | 00/74764 | 12/2000 |
| WO | 2006/121110 | 11/2006 |
| WO | 2009/097660 | 8/2009 |
| WO | 2010/099548 | 9/2010 |

OTHER PUBLICATIONS

Supplementary European Search Report issued Jan. 21, 2014 in corresponding European Application No. EP 11 83 6478.
International Search Report issued Dec. 6, 2011 in International (PCT) Application No. PCT/JP2011/075013.
International Preliminary Report on Patentability and Written Opinion of the International Searching Authority issued May 23, 2013 in International (PCT) Application No. PCT/JP2011/075013.

* cited by examiner

MICRONEEDLE

TECHNICAL FIELD

This invention relates to a microneedle and a microneedle array. More specifically, it relates to a microneedle capable of easily, safely and effectively injecting a chemical, etc., below a skin surface layer or skin cornified layer and a microneedle array.

BACKGROUND ART

Conventionally, almost all methods of administering a chemical, etc., to a patient's living organism surface, i.e., the surface of a skin or a mucous membrane are methods of applying a liquid substance or powder substance. Since, however, the region to which a medical agent can be applied is limited to a skin surface, it is a daily experience to have an applied medical agent come unstuck due to sweating or a contact of a foreign matter, and it has been hence difficult to effectively administer a proper dose of a medical agent, etc.

As the alternative to the application of a medical agent to a living organism surface, there is proposed a method of administering a medical agent into a living organism with a microneedle. Further, there have been so far made proposals to improve the above microneedle in puncturing ability.

For example, Patent Documents 1 and 2 propose microneedles and microneedle arrays that are neither easily bendable nor easily curvable and methods of producing them. However, they have no sufficient puncturing ability.

Patent Document 3 proposes a method in which a surface of a circular cone or surfaces of a pyramid of a microneedle are curved inwardly to make it easily run into. However, the method disclosed in Patent Document 3 is a method that uses a volume contraction when a polymer solution is applied to a stamper and gelation-dried, and it is not suitable for thermoplastic resin.

Patent Document 4 describes a microneedle which is formed from a water-soluble or water-swellable resin and which has the form of a cone, a frustum of cone or "Konide" and has a surface coated with a lubricant component.

(Patent Document 1) JP-A 2007-130030
(Patent Document 2) JP-A 2007-190112
(Patent Document 3) JP-A 2008-142183
(Patent Document 4) JP-A 2010-029634

SUMMARY OF THE INVENTION

It is an object of this invention to provide a microneedle that smoothly runs into a patient's skin surface layer, that has safety and simplicity and that is capable of administering a predetermined dose of a medical agent without causing a pain, and a microneedle array. It is another object of this invention to provide a microneedle that can hold not only a medical agent but also predetermined doses of a stabilizer and a thickener and that has excellent puncturing ability and a microneedle array. It is a further object of this invention to provide a microneedle device including a microneedle array.

According to this invention, the following inventions are provided.

1. A microneedle comprising a frustum and a forward end portion thereon, having a forward end apex angle (A) in the range of 15 to 60° and a forward end diameter (B) in the range of 1 to 20 µm and satisfying the following expression (1), $$H/D \geq 5 \quad (1)$$

(H: Height of the whole, D: Diameter of bottom surface of the frustum).

2. A microneedle as recited in the above paragraph 1, which has a surface roughness represented by the following expression (2), $$5 \text{ nm} \leq Rz \leq 10 \text{ µm} \quad (2)$$

(Rz: a maximum height of surface roughness).

3. A microneedle as recited in the above paragraph 1, which has a surface roughness represented by the following expression (3), $$50 \text{ nm} \leq Rz \leq 5 \text{ µm} \quad (3)$$

(Rz: a maximum height of surface roughness).

4. A microneedle as recited in the above paragraph 1, wherein the whole thereof has a height (H) of 300 to 700 µm and the frustum of cone or pyramid has a bottom surface having a diameter (D) of 10 to 200 µm.

5. A microneedle as recited in the above paragraph 1, which is composed of a thermoplastic resin as a main component.

6. A microneedle as recited in the above paragraph 5, wherein the thermoplastic resin is at least one member selected from the group consisting of polycarbonate, polypropylene, cycloolefin polymer, cycloolefin copolymer, polyethylene terephthalate, acrylic resin, polyphenylene sulfide, polyether ether ketone, polybutylene terephthalate, polybutylene naphthalate and polyethylene naphthalate.

7. A microneedle as recited in the above paragraph 1, which is formed from a biodegradable resin as a main component.

8. A microneedle as recited in the above paragraph 7, wherein the biodegradable resin is at least one member selected from the group consisting of polyglycolic acid, polylactic acid, stereocomplex polylactic acid, polycarbonate resin derived from a plant and polybutylene succinate.

9. A microneedle array comprising a plurality of microneedles recited in the above paragraph 1 and a substrate, wherein the microneedles are arranged on the substrate.

10. A microneedle array as recited in the above paragraph 9, wherein the microneedles are arranged at 50 to 500 microneedles per $cm^2$.

11. A microneedle array as recited in the above paragraph 9, which exhibits puncturing ability of 80% or more when pressed in 10 mm below a skin surface.

12. A microneedle device comprising the microneedle array recited in the above paragraph 9 holding a medical agent, and an applicator for administering the medical agent into a living organism.

13. A method of administering a medical agent, comprising causing the medical-agent-holding microneedle array recited in the above paragraph 9 to run into a skin surface.

EXPLANATION OF SYMBOLS

Figure 1:
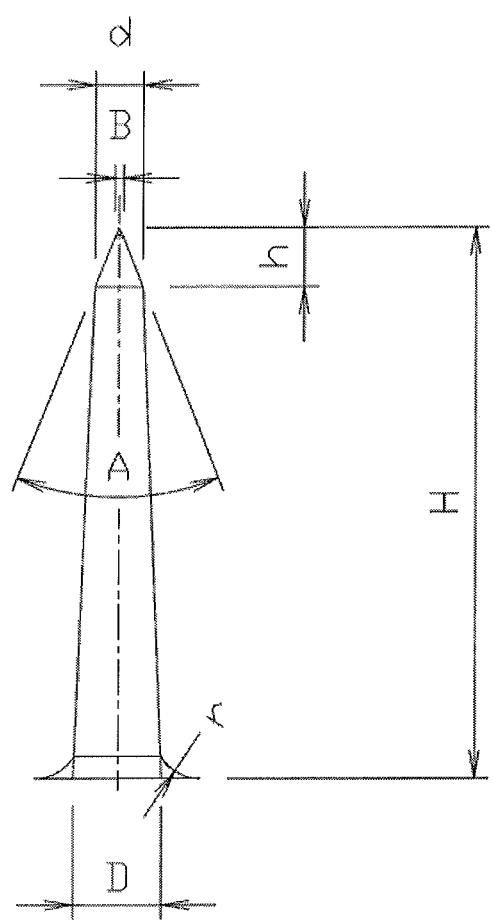
FIG. 1 is a schematic drawing of the microneedle of this invention.

H: Height of the whole
D: Diameter of bottom surface of a frustum
A: Apex angle of a forward end
h: Height of a forward end portion
d: Diameter of bottom surface of a forward end portion
B: Diameter of a forward end
r: Radius of taper
1: Load cell
2: Plunger (φ5 mm)
3: Fixing with a tape
4: Microneedle (φ5 mm)
5: Microneedle
6: Rat skin
7: Expanded polystyrene ((φ30 mm)
8. SHIMAZU Eztest
9. Load cell
10. Plunger (φ5 mm)
11. Pedestal (20 mm×10 mm)
12. Microneedle array (12 mmφ 98 microneedles)
13. Skin model (Upper layer: Rat skin, intermediate layer: SIS 15% 6 mm, lower layer: SIS 30% 9 mm)

DETAILED DESCRIPTION OF THE INVENTION

Figure 2:
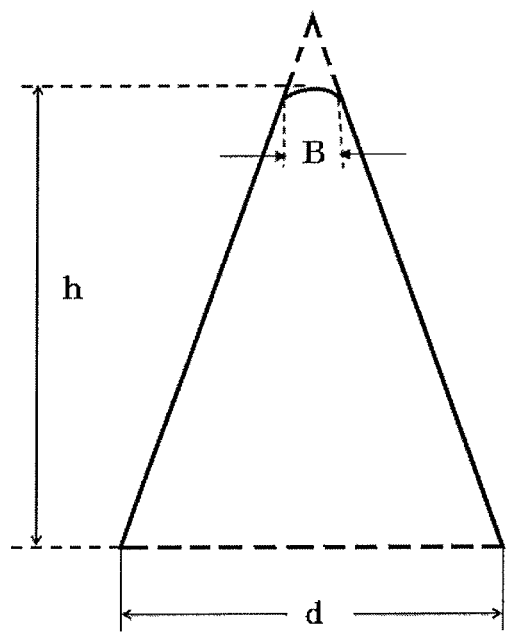
FIG. 2 is a schematic drawing of an apex portion.
Figure 3:
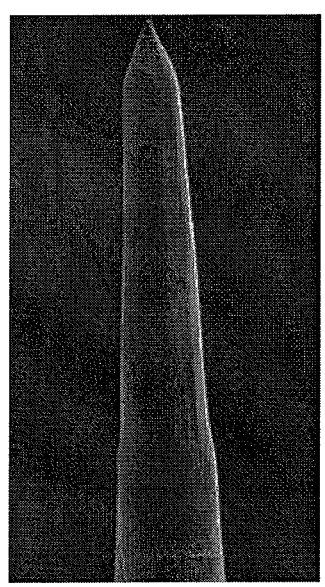
FIG. 3 is a photograph of a microneedle obtained in Example 1.
Figure 4:
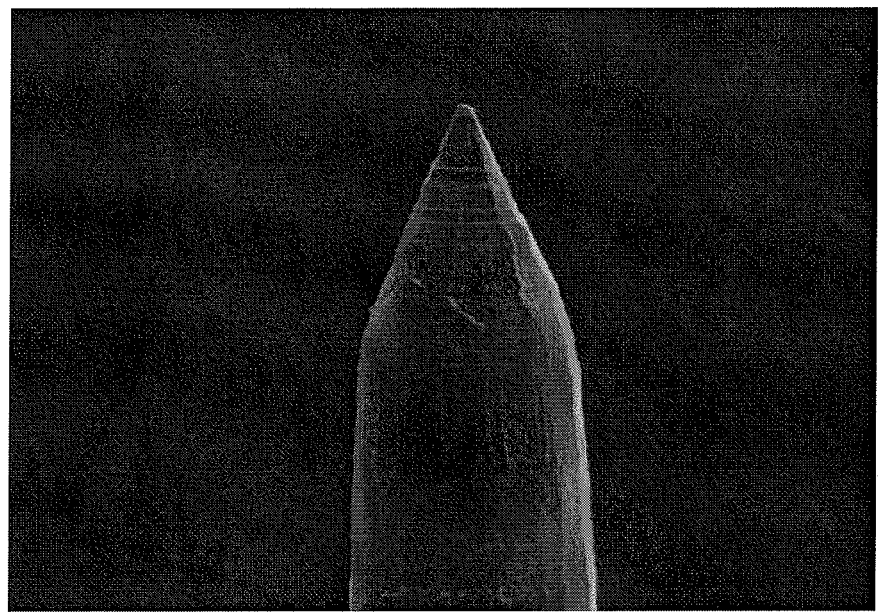
FIG. 4 is a photograph of apex portion of the microneedle obtained in Example 1.

The microneedle of this invention will be explained with reference to FIGS. 1 and 2. FIG. 1 is an overall view of the microneedle. FIG. 2 is an enlarged view of a forward end portion. The microneedle of this invention comprises a frustum and a forward end portion thereon. That is, it has the form of a frustum of a cone or pyramid and a sharper-angled cone or pyramid connected thereto. The frustum of the cone or pyramid may be a frustum of a polygonal pyramid such as a triangular pyramid, a quadrangular pyramid or a frustum of a six-sided pyramid or a frustum of a cone. The forward end portion may have the form of a polygonal pyramid such as a triangular pyramid, quadrangular pyramid or six-sided pyramid.

(Frustum)

The diameter (D) of a bottom surface of the frustum is preferably 10 to 200 μm, more preferably 17 to 200 μm. The diameter (D) of the bottom surface of the frustum of the cone or pyramid is represented by a diameter obtained when the bottom surface of the frustum approximates to a circle.

The height (H-h) of the frustum of the cone or pyramid is obtained by deducting the height (h) of the forward end portion from the total height (H) of the microneedle, and it is preferably 35 to 990 μm, more preferably 75 to 800 μm. The frustum is a frustum of a polygonal pyramid or cone having a bottom surface with a diameter D and an upper surface with a diameter d.

The bottom portion of the frustum may be formed in the form of a pedestal with R or a taper. The size of the R or taper is properly selected such that the needle is not easily broken. In FIG. 1, the bottom portion of a frustum is formed in the form of a pedestal with a taper.

The microneedle of this invention satisfies the following expression (1).

$$H/D \geq 5 \quad (1)$$

(H: Total height of the microneedle, D: Diameter of bottom surface of the frustum).

The upper limit of H/D is preferably 20 or less from the viewpoint of the object of this invention and moldability. When H/D is less than 5, the resistance in puncturing a skin is too greatly increased for a microneedle to run into the skin, and further, the forward end of the microneedle is easily deformed, which are disadvantageous for an object and an effect. H/D is preferably from 5 to 10, more preferably from 5 to 6.

(Forward End Portion)

The diameter (d) of a bottom surface of the forward end portion is preferably 1 to 170 μm, more preferably 10 to 80 μm. The diameter (d) of the bottom surface of the forward end portion is represented by a diameter obtained when the bottom surface of the forward end portion approximates to a circle.

The forward end apex angle (A) is in the range of 15 to 60°, preferably 30 to 60°. When the forward end apex angle (A) is in the range of 30 to 45°, a further excellent effect is found. When the forward end apex angle (A) is outside the range of 15 to 60°, undesirably, the resistance in puncturing a skin is too greatly increased for a microneedle to run into the skin, and further, the forward end of the microneedle is easily deformed.

The forward end diameter (B) is 1 to 20 μm. From the viewpoint of an improvement in the effect of smoothly puncturing a skin surface layer of a patient, the forward end diameter (B) is preferably in the range of 1 to 10 μm. When the forward end diameter (B) exceeds 20 μm, undesirably, the resistance in puncturing a skin is too greatly increased for a microneedle to run into the skin, and the forward end of the microneedle is easily deformed.

The height (h) of the forward end portion is preferably 1 to 640 μm, more preferably 10 to 150 μm.

(Height of the Whole)

The height (H) of the whole is a total sum of a thickness (X) of a skin at which the effect of a medical agent is effectively exhibited and a length (α) of allowance that takes account of the flexibility of a skin when the microneedle is slowly pressed to run into the skin without causing a pain. Specifically, X is preferably 15 to 800 more preferably 100 to 500 μm. Specifically, α is preferably 30 to 500 μm, more preferably 50 to 300 μm.

(Surface Roughness)

The surface roughness of the microneedle is preferably 5 nm≤Rz≤10 μm, more preferably 50 nm≤Rz≤5 μm. When the surface roughness is large, the amount of a medical agent held is desirably increased when a chemical liquid is held. Further, when the surface roughness is large, it has an effect on the prevention of shaping of a sphere caused by the surface tension of liquid of a medical agent when the medical agent is held. The surface roughness should be within the limit that causes a resistance to a mold release during molding which causes deformation, breaking and the deterioration of a yield. The roughness can use impressions formed by machining by design. Rz is a value measured according to JIS B0601-2001.

(Microneedle Array)

In this invention, a microneedle array including a plurality of the above microneedles can be used as such. Since a microneedle array must have two aspects of safety and simplicity and must be able to administer a predetermined medical agent without causing a pain, the density of the microneedles is preferably 50 to 500 microneedles per cm$^2$, more preferably 100 to 500 microneedles per cm². With an increase in the density, the amount of a medical agent held can be increased. However, as the density is increased, it requires a larger force when the microneedles and the microneedle array are pressed to run into a skin. The density is preferably set in a range of the pressing force that causes no pain.

The pressing force is a force required to cause the microneedles and microneedle array to puncture a skin. When it is too large, a patient feels a pain when it is pressed to run into, so that the pressing force is preferably 1 to 200 N, more preferably 1 to 50 N, particularly preferably 1 to 20 N. Since the pressing force is limited, there is required a microneedle that smoothly punctures a skin even with a small load.

When the microneedle array was pressed 10 mm under a skin surface, preferably it exhibits a puncturing ability of 80% or more. Further, when it was pressed a skin by applying a force of 4 to 6 Newton (N) to the substrate having a diameter of 10 mm, preferably, the microneedle array exhibits a puncturing ability of 80% or more.

(Thermoplastic Resin)

The microneedle and microneedle array of this invention are preferably composed of a thermoplastic resin as a main component. The content of the thermoplastic resin in the microneedle and microneedle array is preferably 50% by weight or more, more preferably 90% by weight or more, still more preferably 100% by weight.

The thermoplastic resin preferably includes polycarbonate, polypropylene, a cycloolefin polymer, a cycloolefin copolymer, polyethylene terephthalate or mixtures of these. The thermoplastic resin is preferably a biodegradable resin. The biodegradable resin preferably includes polyglycolic acid, polylactic acid, a stereo complex polylactic acid, a polycarbonate resin derived from a plant or mixtures of these.

The polycarbonate resin derived from a plant refers to a resin composed mainly of a raw material derived from a plant, and it is preferably a polycarbonate resin containing a polycarbonate constituent unit of the following formula (4).

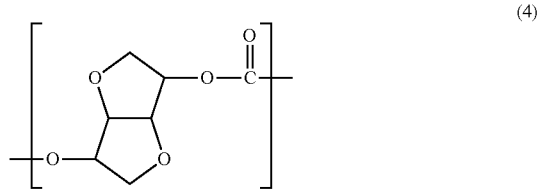

(4)

The polyglycolic acid resin for use in this invention is preferably a homopolymer of glycolic acid composed of glycolic acid recurring units alone, i.e., a glycolic acid homopolymer (PGA, including a ring-opened polymer of glycolide (GL) that is a bimolecular ring-opened ester of glycolic acid). Specifically, it may be a copolymer with other comonomer so long as it maintains 90% by weight or more of the above recurring unit, i.e., a glycolic acid copolymer. The polyglycolic acid preferably has a molecular weight (Mw in terms of a polymethyl methacrylate (weight average molecular weight), measured by GPC measurement using hexafluoroisopropanol, of 100,000 to 800,000, particularly preferably in the range of 130,000 to 750,000. When the molecular weight is too low, the strength of a molded article to be obtained is liable to be insufficient. When it is too high on the other hand, melt extrusion and moldability are sometimes liable to be difficult.

The thermoplastic resin for use in this invention may contain additives such as a stabilizer, a reinforcing agent and a plasticizer. The stabilizer includes an antioxidant, a thermal stabilizer, a hydrolysis-resisting agent, an electron radiation stabilizer and an ultraviolet light stabilizer. As a reinforcing agent, an inorganic filler and an organic filler may be used. As additives, it is preferred to use those that cause no harm to living bodies.

(Method of Producing Microneedle)

The microneedle and microneedle array of this invention can be produced by the following steps. As a molding apparatus, there can be used an apparatus described, for example, in JP 2008-49646A.

(Melting Step)

This step is a step in which a resin is melted by heating it to a temperature range of 200° C. to 300° C.

(Application Step)

This step is a step in which a molten resin is applied to a die that is held at 100° C. to 250° C.

The die is preferably temperature-elevated at a rate of 5° C./second to 10° C./second. In the method of this invention, a resin is applied to a die that is held at 100° C. to 250° C., and after molding, the die temperature is decreased, and a molded article is released from the die. That is, when the molding is continuously carried out, the die repeats the increasing of a temperature and the decreasing of the temperature. Therefore, the greater the rate of increasing and decreasing the temperature is, the cycle time is more advantageously reduced. For accomplishing the above temperature-elevation time, it is preferred to use electromagnetic induction heating. Since the electromagnetic induction heating can implement the local elevation of temperature without increasing the temperature of the entire die, the energy required for molding can be decreased.

(Moldings Step)

This step is a step in which molding is carried out by applying a pressure at 0.1 MPa to 30 MPa and holding the pressure for 5 seconds to 200 seconds.

(Taking-Out Step)

This step is a step in which the temperature is decreased to a temperature range of 50° C. to 100° C. at a rate of 5° C./second to 10° C./second and a molded article is taken out.

In the above method, the time required for increasing the temperature of resin is decreased and a molding time period is decreased as compared with a method of imprinting a film. Further, since a resin uniformly has a predetermined temperature to the inside, highly accurate transfer can be carried out.

For example, there is known a method for producing a molding die in which a die is produced by cutting a metal to form a master and then inverted it by electrocasting so as to produce a die, although the method shall not be limited thereto.

<Microneedle Device>

This invention relates to a microneedle device comprising a microneedle or a microneedle array which hold a medical agent, and an applicator for administering a medical agent to a living organism. The applicator can be selected from known applicators which work by pressing a microneedle array manually or mechanically.

The medical agent includes physiologically active substances such as hormone, vaccine, etc. The medical agent includes growth hormone-releasing hormone (GGRH), growth hormone-releasing factor (GHRF), insulin, insulotropin, calcitonin, octreotide, endorphin, TRN, NT-36

(chemical name: N-[[(s)-4-oxo-2-azetidinyl]carbonyl]-L-histidyl-L-prolineamide), lypressin, hypophyseal hormones (e.g., HGH, HMG, desmopressin acetate, etc.), follicle luteoid, aANF, growth factors such as growth factor releasing factor (GFRF), bMSH, GH, somatostatin, bradykinin, somatotropin, platelet-derived growth factor releasing factor, asparaginase, bleomycin sulfate, chymopapain, cholecystokinin, ciliate gonadotropin, erythropoietin, epoprostenol (antiplatelet drug), glucagon, HCG, bivalirudin, hyaluronidase, interferon α, interferon β, interferon γ, interleukin, interleukin-10 (IL-10), erythropoietin (EPO), granulocyte-macrophage colony stimulating factor (GM-CSF), granulocyte colony stimulating factor (G-CFS), glucagon, luteinizing hormone releasing hormone (LHRH), LHRH analog (goserelin, leyprolide, buserelin, triputorelin, gonadorelin and nafarelin), menotropin (like urofllitropin (FSH and LH)), oxytocin, streptokinase, tissue plasminogen activator, urokinase, vasopressin, deamino [Val4, D-Arg8]arginine vasopressin, desmopressin, corticotrophin (ACTH), ACTH analog like ACTH (1-24), ANP, ANP disappearance repressor, angiotensin II antagonist, antidiuretic hormone agonist, bradykinin antagonist, Ceredase, CSI, calcitonin gene related peptide (CGRP), enkephalin, FAB fragment, IgE peptide inhibitor, IGF-1, neurotrophic factor, colony stimulating factor, parathyroid hormone and agonist, parathyroid hormone antagonist, parathyroid hormone (PTH), PTH analog like PTH (1-34), prostaglandin antagonist, pentigetide, protein C, protein S, renin inhibitor, thimosin α-1, thrombolytic agent, TNF, vasopressin antagonist analog, α-1 antitrypsin (recombinant), and TGF-β.

Further, the medical agent includes protein, polysaccharide complex, oligosaccharide, and antigen in the form of lipoprotein. These subunit vaccine include *bordetella* pertussia (recombinant PT accine-acellular), *clostridium tetani* (purified, recombinant), *corynebacterium* diptheriae (purified, recombinant), cytomegalovirus (glycoprotein subunit), *streptococcus* group A (glycoprotein subunit, complex carbohydrate group A polysaccharide including tetanus toxoide, M protein/peptide combined with toxing subunit carrier, M protein, polyvalent specific epitope, cysteine protease and C5a peptidase), hepatitis B virus (recombinant pre-S1, pre-S2, S and recombinant core protein), hepatitis C virus (recombinant-developed surface protein and epitope), human papilloma virus (capsid protein, TA-GN recombinant proteins L2 and E7 [from HPV-6], MEDI-50I recombinant VLPL1 from HPV-11, tetravalent recombinant BLP L1 [from HPV-6], HPV-11, HPV-16 and HPV-18, and LAMP-E7 [from HPV-16]), *Legionella pneumophila* (purified bacterial surface protein), *neisseria meningitides* (conjugated polysaccharide including tetanus toxoid), *pseudomonas aeruginosa* (synthetic peptide), rubella virus (synthetic peptide), *streptococcus pneumonia* (conjugated polysaccharide combined with BOMP of meningococcus [1,4,5,6B,9N,14,18C,19V,23F], conjugated polysaccharide combined with CRM197 [4,6B,9V,14,18C,19F,23F], conjugated polysaccharide combined with CRM1970 [1,4,5,6B,9V,14,18C,19F,23F]), *treponema pallidum* (surface lipo-protein), varicella zoster virus (subunit, glycoprotein), and *vibrio cholerae* (compounded lipopolysaccharide)

Further, the medical agent includes adrenaline, nicotine, bisphosphonate, fentanyl, etc.

<Method for Administering Medical Agent>

According to this invention, there is provided a method for administering a medical agent, comprising causing the above microneedle or microneedle array holding the medical agent to run into a skin surface. The medical agent includes those which are described above like physiologically active substances and vaccines. The administering method of this invention can be applied to living organisms, and can be also applied to mammals such as cows, swine, humans, etc. According to the administering method of this invention, the microneedle or microneedle array can be caused to run into a skin surface with a smaller force without a pain.

EXAMPLES

Examples of working embodiments will be described below.

Example 1

Microneedles were produced as follows.
(Die)

For a die, a metal was machined by cutting it to make a master for a die, and the master die was inverted by nickel electrocasting to make a die. In the form of a microneedle, the microneedle had a forward end diameter of 7 μm, the whole had a height (H) of 600 μm, the bottom surface of frustum of cone had a diameter (D) of 100 μm, a forward end apex angle of 45°, and 97 microneedles were made.
(Die-Forming)

For forming the microneedles, a melt fine transfer apparatus (registered trademark) supplied by Japan Steel Works, Ltd. was used.

For a resin, polyglycolic acid was used, and it was melted at 260° C. and a molten resin was applied to a die at 200° C. Then, the resin was pressed at a pressure of 20 MPa for approximately 30 seconds, and then the die was cooled to 80° C. to give a microneedle array from the die.

The thus-obtained microneedle array was observed through a scanning electron microscope to confirm that the form of the mold was accurately transferred without any breaking or deformation. Then, the microneedle array was evaluated for puncturing ability. Table 1 shows the results. After the above test, the microneedle array was evaluated for easiness in breaking of forward ends. Table 1 shows the results.

Example 2

A microneedle array was produced in the same manner as in Example 1 except that the form thereof was changed as shown in Table 1. Table 1 shows the evaluation results.

Example 3

A microneedle array was produced in the same manner as in Example 1 except that the form thereof was changed as shown in Table 1. Table 1 shows the evaluation results.

Comparative Example 1

A microneedle array was produced in the same manner as in Example 1 except that the form thereof was changed as shown in Table 1. Table 1 shows the evaluation results.

Comparative Example 2

A microneedle array was produced in the same manner as in Example 1 except that the form thereof was changed as shown in Table 1. Table 1 shows the evaluation results.

Comparative Example 3

A microneedle array was produced in the same manner as in Example 1 except that the form thereof was changed as shown in Table 1. Table 1 shows the evaluation results.

TABLE 1

|  | Ex. 1 | Ex. 2 | Ex. 3 | CEx. 1 | CEx. 2 | CEx. 3 |
|---|---|---|---|---|---|---|
| Forward end diameter: B (μm) | 7 | 20 | 7 | 7 | 7 | 100 |
| Height of forward end portion: h (μm) | 64 | 64 | 45 | 64 | 25 | 50 |
| Height of the whole: H (μm) | 600 | 600 | 600 | 600 | 600 | 600 |
| Diameter of bottom surface of frustum: D (μm) | 100 | 100 | 100 | 300 | 100 | 100 |
| H/D (—) | 6 | 6 | 6 | 2 | 6 | 6 |
| Forward end apex angle: A (°). | 45 | 45 | 60 | 45 | 90 | 45 |
| Diameter of bottom surface of forward end portion: d (μm) | 53 | 53 | 52 | 53 | 50 | 100 |
| Puncturing ability | ○ | ○ | ○ | Δ | Δ | X |
| Easiness in breaking | ○ | ○ | ○ | Δ | Δ | X |

Ex. = Example,
CEx. = Comparative Example
○: Good
Δ: Slightly poor
X: Poor

Evaluations

Microneedles obtained in Examples 1-3 and Comparative Examples 1-3 were evaluated by the following tests.

(Evaluation 1) Evaluation of Puncturing Ability Based on Form a) Materials:

Evaluation Sample

For evaluating the microneedles obtained in Examples 1-3 and Comparative Examples 1-3 for puncturing ability based on the form of the microneedles, single-needle microneedles made of stainless steel having the same forms as those of the microneedles obtained in Examples 1-3 and Comparative Examples 1-3 were produced. The microneedles made of stainless steel were produced by cutting predetermined forms on one end surface of each of SUS304 rods having a diameter of 3 mm with a fine forming machine (Rokuroku Sangyo "MEGA-S400").

Skin Model:

An abdominal part skin of a Wistar rat (age 5 weeks, male) was set on an arc of a semispherical expanded polystyrene (φ30 mm).

Machine for Use:

Bench tension and compression tester (Ez-test, Shimadzu Corporation)

Plunger φ5 mm (Shimadzu Corporation)

Load cell 10N (Measurement resolution 1/20000, Shimadzu Corporation)

Figure 5:
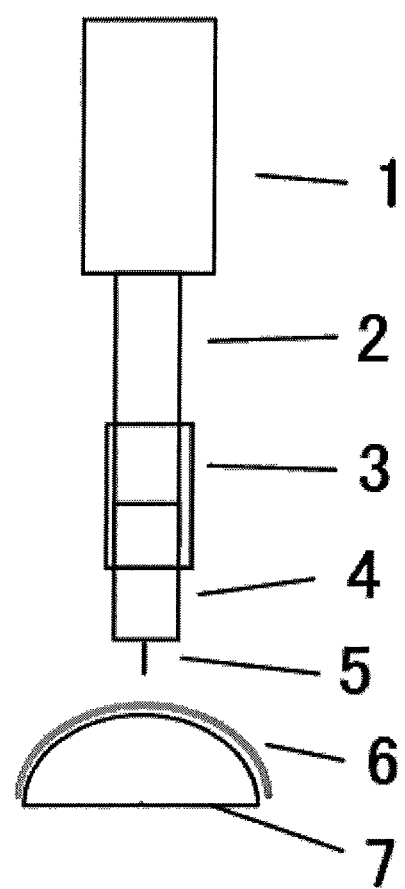
FIG. 5 is a schematic drawing of an apparatus for evaluating puncturing ability.

Digital microscope (Keyence VHX-1000)

b) Evaluation Method:

As shown in FIG. 5, a needle was fixed to the top end of the plunger with a tape. A drop of a 2% gentian violet Et-OH solution was caused to fall on the top end of the needle attached to the plunger to stain it. The plunger with the needle attached thereto was set in the bench tension and compression tester (Ez-test), and it was arranged that the top end of the needle was in contact with the rat skin. That position was used as a point zero.

The needle was moved in the skin model up to a set stress at a rate of 1 mm/minute. After the set stress was reached, the needle was caused to retreat from the skin model at a rate of 1 mm/minute.

Then, the needle was removed, and the materials were allowed to stand for approximately 1 minute. The punctured portion of the rat skin was washed with Et-OH, the dye (gentian violet) on the skin was cleaned, and then punctured portion was observed for a punctured mark with a digital microscope. The puncturing test was carried out three times per one needle for conducting the evaluation.

Symbols in FIG. 5 show the following.

1. Load cell
2. Plunger (φ5 mm)
3. Being fixed with a tape
4. Microneedle (φ5 mm)
5. Microneedle
6. Rat skin
7. Expanded polystyrene (φ30 mm)

c) Evaluation Results:

The needle was pressed to the rat skin until the set stress was reached, and it was evaluated whether or not the skin was punctured to be stained with the gentian violet. The skin was punctured three times, and when it was not punctured, such was expressed as 0/3, and when it was punctured three times, such as expressed as 3/3. The following Table 2 shows the results.

TABLE 2

| Puncture stress (N) | Ex. 1 | Ex. 2 | Ex. 3 | CEx. 1 | CEx. 2 | CEx. 3 |
|---|---|---|---|---|---|---|
| 0.01 | 1/3 | 0/3 | 0/3 | 0/3 | 0/3 | 0/3 |
| 0.02 | 2/3 | 0/3 | 2/3 | 2/3 | 0/3 | 0/3 |
| 0.03 | 3/3 | 0/3 | 3/3 | 3/3 | 0/3 | 0/3 |
| 0.05 | 3/3 | 2/3 | 3/3 | 3/3 | 0/3 | 0/3 |
| 0.1 | 3/3 | 3/3 | 3/3 | 3/3 | 2/3 | 0/3 |

Ex. = Example,
CEx. = Comparative Example

When the forward end had a diameter of 7 μm, the microneedles of Examples 1 and 3 had the same puncturing ability although their apex angles were different like 45° and 60°. However, the microneedle of Comparative Example 2 showed extremely poor puncturing ability when its forward end had an apex angle of 90° although it had a forward end diameter of 7 μm. The microneedle of Example 2 had poor puncturing ability since it had a forward end diameter of 20 μm although its forward end angle was 45°.

(Evaluation 2) Dose of Medical Agent Held

Figure 10:
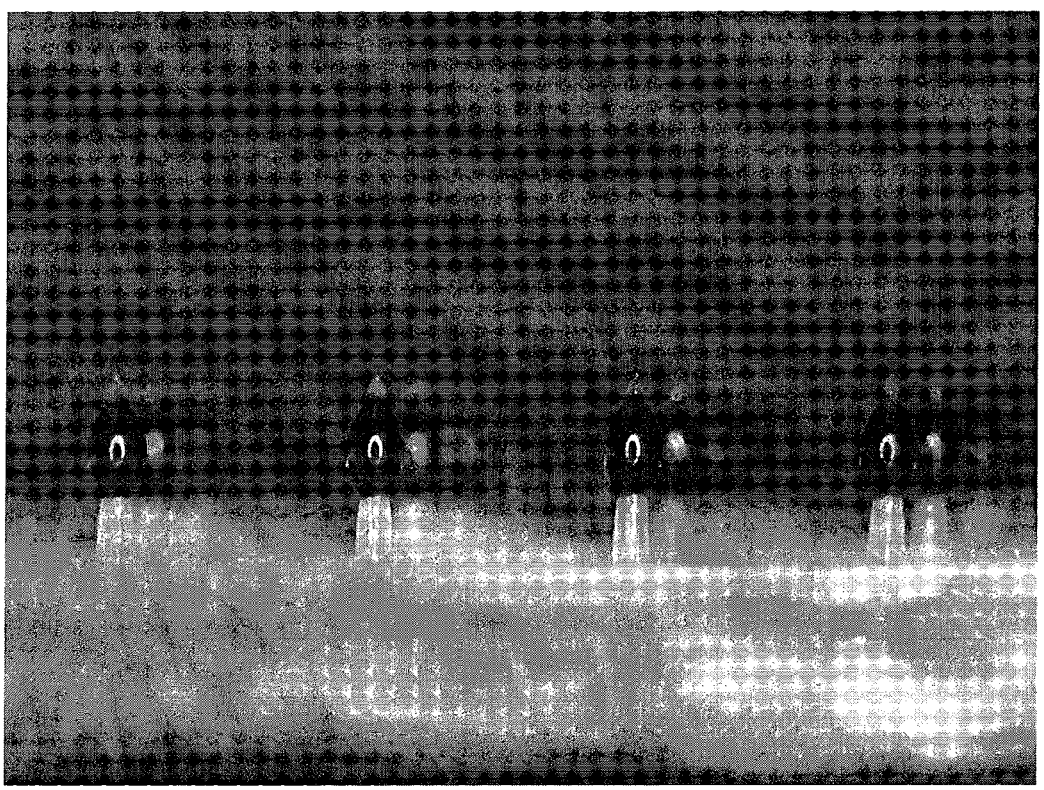
FIG. 10 is a showing of a microneedle array image after a medical agent is held.

FIG. 10 shows an image of the microneedle of Example 1 that holds a medical agent. If this form is maintained, the dose of the medical agent held thereon can be secured while maintaining sharpness.

The capability of holding the medical agent (needle form: Height H/D) was evaluated by three stages based on the value of H/D.

Index 3: 5 or more, index 2: 4 or more but less than 5, index 1: less than 4

Further, as an index for puncturing ability, puncture stresses at which puncturing was enabled 100% were evaluated by the following four stages.

Index 3: Less than 0.05 N/needle, index 2: less than 0.1 N/needle, index 1: 1.0 N/needle or more, index 0: cannot be punctured.

A comprehensive evaluation was made on the basis of an index for capability of holding the medical agent x index for puncturing ability. Table 3 shows the results. As is clear from the comprehensive evaluation in Table 3, it is made clear that the forms of Examples 1-3 are suitable as the form of the microneedle.

TABLE 3

|  | Ex. 1 | Ex. 2 | Ex. 3 | CEx. 1 | CEx. 2 | CEx. 3 |
|---|---|---|---|---|---|---|
| Capability of holding medical agent (needle form: height H/D) | 3 | 3 | 3 | 1 | 3 | 3 |
| Puncturing ability | 3 | 2 | 3 | 3 | 1 | 0 |
| Comprehensive evaluation | 9 | 6 | 9 | 3 | 3 | 0 |

Ex. = Example,
CEx. = Comparative Example (Evaluation 3) Evaluation of Puncture Depth Depending Upon Difference in Form There were produced single-needle microneedles made of stainless steel having the same forms as those of the microneedles obtained in Example 1 and Comparative Example 1. The microneedles made of stainless steel were produced by cutting predetermined forms on one end surface of each of SUS304 rods having a diameter of 3 mm with a fine forming machine (Rokuroku Sangyo "MEGA-S400").

a) Evaluation Method

Single-needle microneedles having the same forms as those of the microneedles obtained in Example 1 and Comparative Example 1 were immersed in a dye liquid (PVPK-30 20% and Brilliant Blue 3%) to make dye liquid adhere thereto. The adhering liquids were air-dried, and the dye liquid was again made to adhere similarly. These procedures were repeated 3 to 5 times to coat the microneedles with the dye liquid.

The needle coated with the dye liquid was fixed to the top end of a plunger with a tape. The plunger with the needle attached thereto was set on a bench tensile-compression tester (Ez-test), and it was arranged that the top end of the needle was in contact with a rat skin. That position was used as a point zero. Then, the needle was moved in the skin model at a rate of 1 mm/minute up to a set stress of 0.03 N. After the set stress of 0.03 was reached, the needle was fixed in that state and allowed to stand for 1 hour. On an average, the needle stopped in a position where it moved approximately 200 μm from the position of zero point. Then, the needle was caused to retreat from the skin model at a rate of 1 mm/minute and removed from the skin.

The removed needle was observed through a digital microscope to evaluate how far from the top end the dye on the needle came off (decoloring depth). The puncturing test was carried out twice for each needle, and the length of the needle that was decolored was evaluated as a depth of puncturing of the needle in the skin.

b) Evaluation Results

The degree of puncture depths in the skin (puncturing depth) depending upon differences in the forms of the microneedles of Example 1 and Comparative Example 1 were evaluated, and summarized in the following Table 4.

TABLE 4

| Stress (N) | Example 1 | Comparative Example 1 |
|---|---|---|
| 0.03 | 85.5 μm | 54.9 μm |

As shown in the above Table 4, the width of the needle is as small as an H/D of 6 in Example 1, while that of the needle in Comparative Example 1 is as large as an H/D of 2, so that the needle of Comparative Example 1 is too large to run into the skin. As compared with the needle having the form of Example 1, the entering depth of the needle having the form of Comparative Example 1 into the skin was 64.2% of that of the needle of Example 1 (54.9 μm/85.5 μm).

(Evaluation 4) Medical Agent Administering Evaluation

Needle tips of microneedle arrays obtained in Example 7 were immersed in a 40% ovalbumin (OVA) aqueous solution to apply it to them such that a dry OVA amount per each array was 50 μg, and they were used as samples for inoculation.

Abdominal parts of mice Nos. 1-5 were defurred, the sample surfaces with needles for inoculation were pressed thereto, kept pressing for 30 seconds and then fixed with a tape each, and they were held for 30 minutes. The samples for inoculation were removed, and the mice were raised for 2 weeks and then again inoculated similarly. For antibody titers (IgG) in blood before the test and 5 weeks after the test, UV absorbance values were measured by an Elisa test.

(Control)

Mice Nos. 6-10 were inoculated with a 50 μg/0.2 ml OVA aqueous solution by subcutaneous injection, raised for 2 weeks and then additionally inoculated with the same dose of the OVA aqueous solution. For antibody titers (IgG) in blood before the test and 5 weeks after the test, UV absorbance values were measured by an Elisa test. The following Table 8 shows the results.

TABLE 8

| Administering by microneedle array | | | | | | |
|---|---|---|---|---|---|---|
| | Mouse No. | | | | | |
| | 1 | 2 | 3 | 4 | 5 | Average |
| Before inoculation | 0.006 | 0.002 | 0.003 | 0.001 | 0.00035 | 0.0031 |
| 6 weeks after inoculation | 1.157 | 1.972 | 2.324 | 1.349 | 1.184 | 1.5972 |
| Administering by subcutaneous injection | | | | | | |
| | Mouse No. | | | | | |
| | 4 | 5 | 6 | 7 | 8 | Average |
| Before inoculation | 0.0025 | 0.004 | 0.002 | 0.000 | 0.0065 | 0.003125 |
| 6 weeks after inoculation | 0.395 | 0.243 | 0.565 | 0.775 | 1.241 | 0.706 |

Examples 4 and 5

Microneedle arrays (97 needles each) shown in the following Table 5 were produced from a polyglycolic acid resin. It was evaluated by the following method how the puncture efficiency of the microneedle arrays (97 needles) would change depending upon the size of the needles (H/D).

In the above evaluation 3, the entering depths of the needles into the skin differ depending upon the sizes of the needles (H/D). It was hence evaluated how the puncturing efficiency of the microneedle array (97 needles) would change depending upon the size of the forward end portions of the needles (h/d).

a) Materials:

Evaluation Sample

Microneedle arrays (97 needles) shown in the following Table 5 were used for evaluation.

Human Skin Model:

A 6-mm thick sheet was formed by melting 30% of SIS and 70% of liquid paraffin under heat and set, and further, a 9-mm thick sheet was formed by melting 15% of SIS and 85% of liquid paraffin under heat and stacked thereon to prepare a substrate of two layers. An abdominal part skin of Wister rat (male, 5 weeks) was set on the substrate to prepare a human skin model.

Machine for Use:

The same machine as that in Evaluation 1 was used.

b) Evaluation Method

Figure 6:
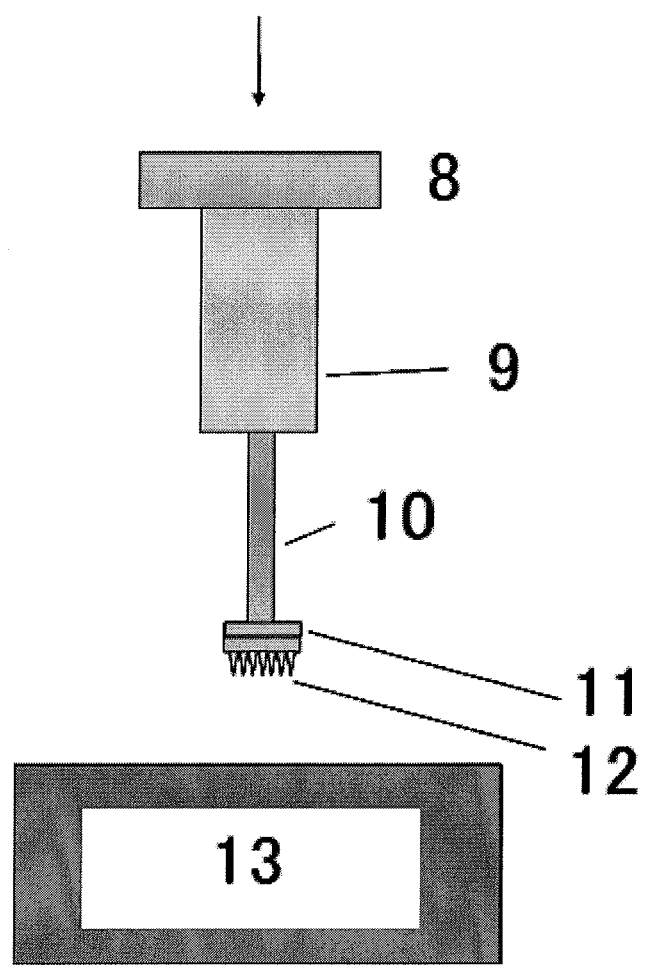
FIG. 6 is a schematic drawing of an apparatus for evaluating puncturing ability.

A small bench tester (Ez-test) shown in FIG. 6 was used, a plunger (φ5 mm) was set on its load cell, and further, a polypropylene (PP) plate (pedestal 12 mmφ, 0.8 mm thick) was attached to its forward end. Further, the microneedle array was set on the PP plate. The forward end portions of the needles were dyed with a 2% gentian violet ET-OH solution.

The needle forward end portions of the above microneedles were brought into contact with the skin surface of the above human skin model, and the needles were moved a set distance of 10 mm at a rate of 60 mm/minute to be pressed into the skin model.

With regard to the rat skin of the human skin model surface, portions where holes were punctured in the skin with the microneedle array were colored with the gentian violet to turn purple. Therefore, colored portions were visually counted, and the puncturing efficiency (number of colored portions/number of needles) of each microneedle array was evaluated.

Symbols in FIG. 6 indicate the following.
8. SHIMAZU Eztest
9. Load cell
10. Plunger (φ5 mm)
11. Pedestal (12 mmφ)
12. Microneedle array (12 mmφ, 97 needles)
13. Skin model (Upper layer: rat skin, intermediate layer: SIS 15%, 6 mm, lower layer: SIS 30%, 9 mm)

c) Evaluation Results

The puncturing efficiency of the microneedle arrays was determined, and Table 5 shows the results.

TABLE 5

|  | Example 4 | Example 5 |
|---|---|---|
| Forward end diameter: B (μm) | 7 | 10 |
| Height of forward end portion: h (μm) | 64 | 135 |
| Height of the whole: H (μm) | 600 | 600 |
| Diameter of bottom surface of frustum: D (μm) | 100 | 180 |
| H/D (—) | 6 | 3.3 |
| Forward end apex angle: A (°) | 45 | 40 |
| Diameter of bottom surface of forward end portion: d (μm) | 53 | 100 |
| h/d (—) | 1.2 | 1.4 |
| Number of needles | 97 | 97 |
| Puncturing ability (puncturing efficiency) | >90% | 40 to 60% |

As is clear in Table 5, it is shown that with an increase in H/D (as the needles get smaller in size), the puncturing efficiency is higher. When the pedestal (substrate) was 10 mmφ, the stress when the needles were pressed 10 mm deep in the above skin model was in the range of 4 to 6 N, and when the pedestal was 12 mmφ, that was 6 to 9 N.

Example 6

A microneedle array (97 needles) shown in the following Table 6 was produced from a polyglycolic acid in the same manner as in Example 1. The puncturing depth when the 97-needle microneedle array (φ13 mm) was pressed was evaluated by the following method.

a) Materials:
Human Skin Model:

A 6-mm thick sheet formed by melting 30% of SIS and 70% of liquid paraffin under heat was set, and further, a 9-mm thick sheet formed by melting 15% of SIS and 85% of liquid paraffin under heat was stacked thereon to prepare a substrate of two layers. An abdominal part skin of Wister rat (male, 5 weeks) was folded in two such that the abdominal part skin faced outward and set on the substrate.

Machine for Use:

The same machine as that in Evaluation 1 was used.

b) Evaluation Method:

Blue No. 1 (3%) was dissolved in a 20% PVP K30 aqueous solution to prepare a solution, and the forward ends of the above microneedle array were immersed therein three times to color the needle surfaces.

The microneedle array was set above on the human skin model such that the forward ends of needles faced downward. The microneedle array was fixed above the skin with a surgical tape (25 mm×20 mm) thereon. The microneedle array was pressed with a plunger (5 mmφ) using a bench small tester (Ez-test) on the surgical tape by a distance of 10 mm as described above.

After the pressing, the plunger was lifted up, and the microneedle array was allowed to stand at room temperature for 4 hours while it was fixed with the tape. Then, the microneedle array was recovered, and it was observed and evaluated with a digital microscope how far in position the coloring of the needles came off.

c) Evaluation Results

When the microneedle array was carefully examined with a digital microscope for how the coloring remained, there was no difference in entering depth of the needles into the skin between the surrounding part and central part of the microneedle array. It was shown that similar entering depths of the needles were obtained in the whole of the microneedle array.

Figure 7:
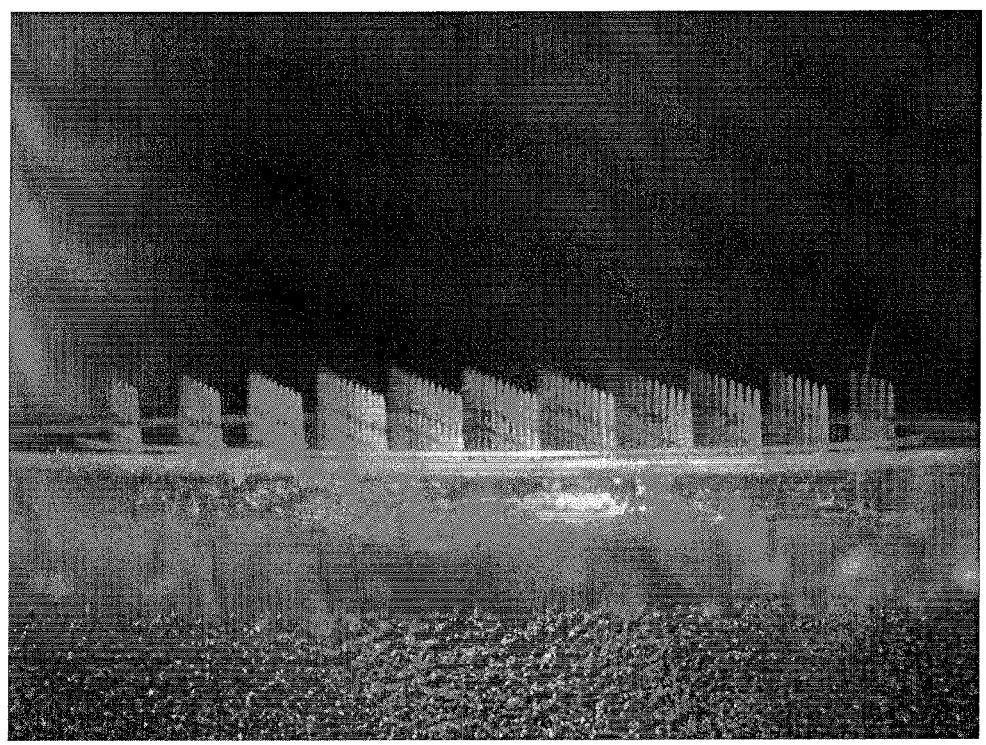
FIG. 7 is a photograph of a microneedle array after puncturing (30 magnifications).
Figure 8:
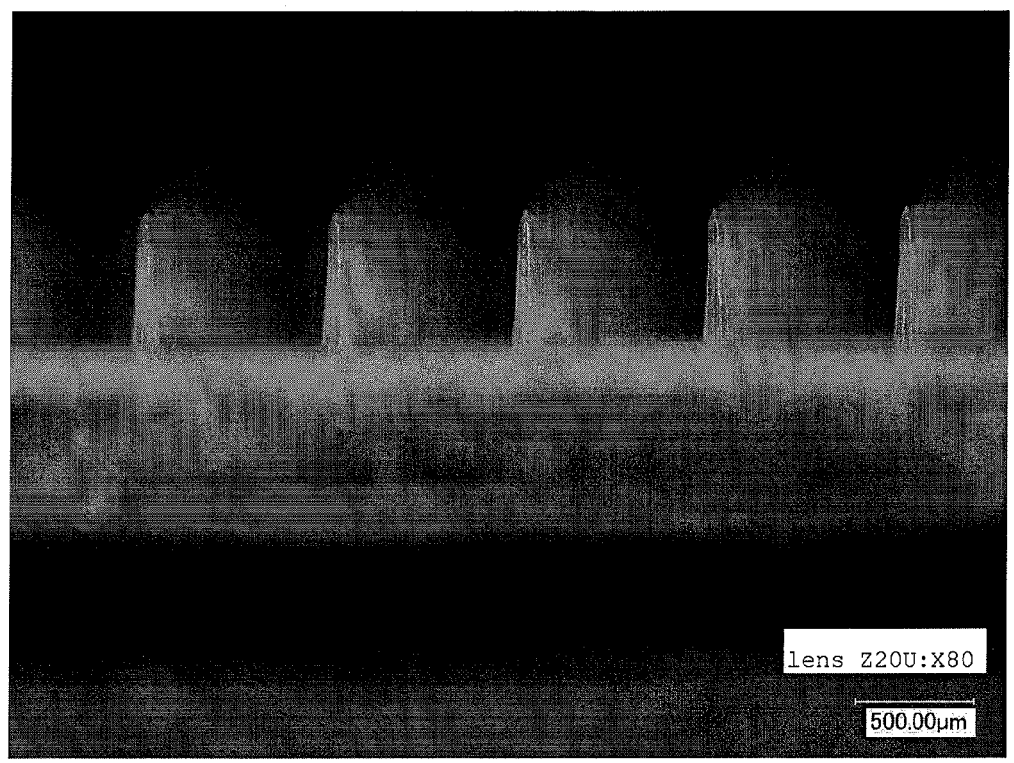
FIG. 8 is a photograph of a microneedle array after puncturing (80 magnifications).
Figure 9:
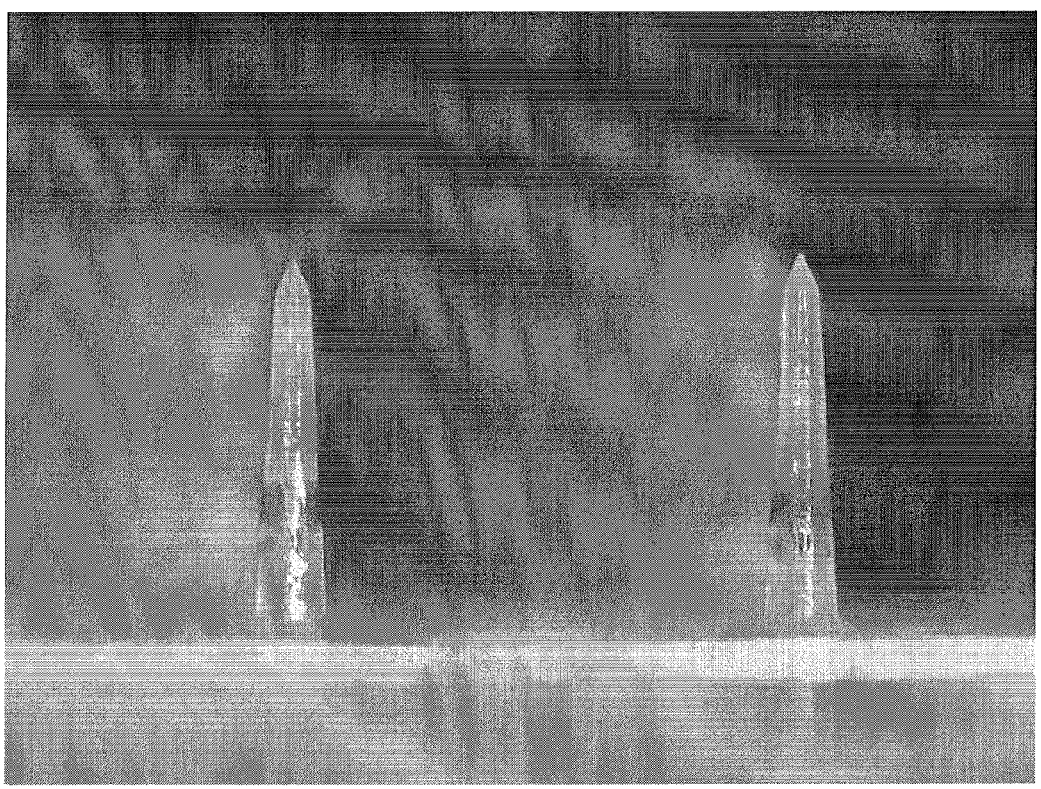
FIG. 9 is a photograph of a microneedle array after puncturing (1200 magnifications).

FIGS. 7 to 9 show photographs of the microneedle array after their puncturing. Since those portions of the needles which extended from the forward end portions thereof to portions where the blue coloring remained showed that the needles punctured the skin, these images showed that the entering depth of the needles into the skin was approximately 335 μm as an average.

TABLE 6

|  | Example 6 |
|---|---|
| Forward end diameter: B (μm) | 7 |
| Height of forward end portion: h (μm) | 64 |
| Height of the whole: H (μm) | 600 |
| Diameter of bottom surface of frustum: D (μm) | 100 |
| H/D (—) | 6 |
| Forward end apex angle: A (°) | 45 |
| Number of needles | 97 |
| Puncturing ability (puncturing efficiency) | >90% |

Examples 7 and 8

A die comprising microneedles having an increased surface roughness was produced, and a microneedle array (97 needles) having a form shown in the following Table 7 was produced from a polyglycolic acid resin in the same manner as in Example 1 (Example 7). Further, a die comprising microneedles having a decreased surface roughness was produced, and a smooth microneedle array having a small surface roughness was produced (Example 8). The surface roughness (Rz) was measured with an ultra-precision non-contact three-dimensional surface property measuring apparatus Talysurf CCI6000 supplied by Taylor Hobson.

For evaluating a correlation of the surface roughness of microneedles and affinity between microneedles and a medical liquid, it was evaluated by the following method how far needles surfaces were wet when the forward end portions of the microneedles were immersed a predetermined depth in the medical liquid.

a) Evaluation Sample:

The microneedle arrays obtained in Examples 7 and 8 were evaluated.

b) Evaluation Method:

An aqueous solution containing 15% of PVP K90 and 2% of Blue No. 1 was prepared, and the prepared solution was filled in a 400 μm deep groove. The microneedle arrays were vertically immersed in the groove, and when the forward ends of the needles were immersed in the solution by 150 μm, the immersion was stopped. Then, the microneedle arrays were taken up, and after the medical solution dried, distances from the forward ends of the microneedle, where the medical solution adhered as shown in FIG. 8, were observed through a digital microscope. Table 7 shows an average of distances of portions dyed with a blue color (portions wetted with the medical solution) adhering to the outermost needles (5 to 6 needles).

c) Test Results

It has been seen that the degree of wetting with the medical solution differs as shown in the following Table 7 depending upon a difference in the surface roughness of the above microneedle arrays.

As shown in Table 7, it has been seen that the roughened surfaces of the needles are improved over the smooth surfaces of the needles in wettability (wettability to the medical solution) by about 17% ((141-121)/121). That is, it has been shown that the microneedle array having a surface roughened to some extent (50 nm or more) has a larger medical agent holding.

TABLE 7

|  | Example 7 | Example 8 |
|---|---|---|
| Forward end diameter: B (μm) | 7 | 7 |
| Height of forward end portion: h (μm) | 64 | 64 |
| Height of the whole: H (μm) | 600 | 600 |
| Diameter of bottom surface of frustum: D (μm) | 100 | 100 |
| H/D (—) | 6 | 6 |
| Forward end apex angle: A (°) | 45 | 45 |
| Number of needles | 97 | 120 |
| Surface roughness: Rz (nm) | 308 | 93 |
| Height of wetting with medical agent (μm) | 141 | 121 |

Effect of the Invention

The microneedle and microneedle array of this invention run into the skin surface layer of a patient only by pressing them with fingers, have both aspects of safety and easiness to use, and can administer a predetermined dose of a medical agent without causing a pain.

INDUSTRIAL APPLICABILITY

The microneedle of this invention can be applied not only to medical treatment but also to MEMS devices requiring a fine needle-like structure, drug discovery, and cosmetics.

The invention claimed is:

1. A microneedle comprising:
    a frustum of a cone or pyramid, wherein a diameter D of a bottom surface of the frustum is larger than a diameter of an upper surface of the frustum;
    a flange at a bottom portion of the frustum; and
    a forward end portion formed on the upper surface of the frustum, wherein the forward end portion has a forward end apex angle (A) in a range of 15 to 60° and a forward end diameter (B) in a range of 1 to 20 μm and satisfying the following expression (1), $$H/D \geq 5 \quad (1)$$

where H is a total height of the microneedle,
the frustum having a first taper, and
the flange having a second taper shallower than the first taper.

2. The microneedle of claim 1, which has a surface roughness represented by the following expression (2), $$5 \text{ nm} \leq Rz \leq 10 \text{ μm} \quad (2)$$

where Rz is a maximum height of the surface roughness.

3. The microneedle of claim 1, which has a surface roughness represented by the following expression (3), $$50 \text{ nm} \leq Rz \leq 5 \text{ μm} \quad (3)$$

where Rz is a maximum height of the surface roughness.

4. The microneedle of claim 1, wherein the height H is 300 to 700 μm and the diameter D of the bottom surface of the frustum is 10 to 200 μm.

5. The microneedle of claim 1, wherein the microneedle is comprised of a thermoplastic resin.

6. The microneedle of claim 5, wherein the thermoplastic resin is at least one member selected from the group consisting of polycarbonate, polypropylene, cycloolefin polymer, cycloolefin copolymer, polyethylene terephthalate, acrylic resin, polyphenylene sulfide, polyether ether ketone, polybutylene terephthalate, polybutylene naphthalate and polyethylene naphthalate.

7. The microneedle of claim 1, wherein the microneedle is comprised of a biodegradable resin.

8. The microneedle of claim 7, wherein the biodegradable resin is at least one member selected from the group consisting of polyglycolic acid, polylactic acid, stereocomplex polylactic acid, polycarbonate resin derived from a plant and polybutylene succinate.

9. A microneedle array comprising a plurality of microneedles recited in claim 1, and a substrate, wherein the plurality of microneedles are arranged on the substrate.

10. The microneedle array of claim 9, wherein the microneedles are arranged at 50 to 500 microneedles per cm$^2$.

11. The microneedle array of claim 9, wherein the microneedle array exhibits a puncturing efficiency of 80% or more when pressed on a skin surface sufficient to form a dent in the skin surface 10 mm deep.

12. A microneedle device comprising the microneedle array recited in claim 9 holding a medical agent, and an applicator for administering the medical agent into a living organism.

13. A method of administering a medical agent with the microneedle array according to claim 9, the microneedle array holding the medical agent, the method comprising causing the medical-agent-holding microneedle array to puncture a skin surface.

14. The microneedle of claim 1, wherein the microneedle is configured to deliver a drug to a target area from a surface of the microneedle.

15. The microneedle of claim 1, wherein H is no more than 700 μm.

16. The microneedle of claim 1, wherein the microneedle is solid.

17. The microneedle of claim 1, wherein the first taper is a constant taper.

* * * * *